United States Patent [19]

Coleman et al.

[11] 4,426,418
[45] Jan. 17, 1984

[54] LUBRICATED TISSUE

[75] Inventors: Michael G. Coleman, Tempe; Israel A. Lesk, Scottsdale, both of Ariz.

[73] Assignee: Harry M. Weiss, Phoenix, Ariz.

[21] Appl. No.: 285,418

[22] Filed: Jul. 20, 1981

Related U.S. Application Data

[63] Continuation of Ser. No. 591,558, Jun. 30, 1975, abandoned.

[51] Int. Cl.$^3$ .................. A61M 35/00; B32B 3/10; B32B 29/06; C11D 17/06
[52] U.S. Cl. .................. 428/211; 15/104.93; 252/91; 252/92; 424/16; 424/27; 428/537
[58] Field of Search .................. 252/91, 92; 424/16, 424/27; 427/286, 288; 428/43, 211, 537, 906, 156; 120/260-262; 15/104.93

[56] References Cited

U.S. PATENT DOCUMENTS 1,168,254  1/1916  Frisch et al. .................. 427/288
3,814,096  6/1974  Weiss et al. .................. 428/28

Primary Examiner—Bruce H. Hess
Attorney, Agent, or Firm—Harry M. Weiss

[57] ABSTRACT

An improved lubricated tissue consists of a sheet of absorbent paper and an array of regions of the absorbent paper impregnated with a lubricating material. The impregnated regions each have a size that is small in comparison to the size of the tissue. The array is arranged in a substantially uniform manner throughout said sheet. Thus, the regions of the array are at least substantially surrounded by absorbent paper free of lubricating materials.

4 Claims, 3 Drawing Figures

LUBRICATED TISSUE

This application is a continuation of application Ser. No. 591,558, filed June 30, 1975, now abandoned.

FIELD OF THE INVENTION

This invention relates to an improved tissue especially adapted for facial and other personal care uses. More particularly, the invention relates to an improved form of lubricated tissue of the general type disclosed in Weiss et al, U.S. Pat. No. 3,814,096.

DESCRIPTION OF THE PRIOR ART

The above Weiss et al patent discloses the basic concept of a lubricated tissue, in which the tissue has a dry portion for absorbency and a portion or portions impregnated with a lubricated material for applying a soothing or medicated coating to portions of the face or body. In the embodiments there disclosed, the lubricated portions of the tissue are located along the sides of the tissues, under a fold-over flap in order to prevent the tissues from sticking together as packaged.

While such a tissue is very effective for applying the lubricating material to an irritated portion of the body, these embodiments require that the user employ one part of the tissue for absorbency and another part of the tissue for applying the lubricating material. From the standpoint of the user, it would be more convenient if the user need not concern himself with which area of the tissue he is using for a particular purpose.

The lubricated tissue embodiments disclosed in the Weiss et al patent further present some difficulties in manufacturing. The manufacture of facial tissues follows common practice in the paper industry. That is, the paper from which the tissues are made is fabricated in large rolls which are then cut up to provide the individual tissue sheets. In order to fabricate the prior art lubricating tissue embodiments by such techniques, it would be necessary either to apply the lubricating material to the tissues after they have been cut into sheets or to register the deposits on the large rolls fairly precisely so that they would end up in the proper position on the individual sheets after they have been cut. Either approach adds considerable complexity to tissue manufacture.

SUMMARY OF THE INVENTION

Accordingly, it is an object of this invention to provide an improved lubricated tissue in which the user may obtain both absorbency from the tissue and application of the lubricating material to the body without using different portions of the tissue for these two purposes.

It is another object of this invention to provide a tissue in part impregnated with a medicated or soothing lubricating material, which tissue can be made using high speed techniques conventionally employed in tissue fabrication.

It is still another object of the invention to provide an improved lubricated tissue in which it is not necessary to use separate parts of the tissue for absorbency and applying lubricating material to the body, yet which will not cause the tissues to stick together when packaged.

The attainment of these and related objects may be achieved through use of the improved lubricated tissue herein disclosed. A tissue in accordance with this invention has a sheet of absorbent paper and an array of regions of the sheet which are impregnated with a lubricating material, each of the regions being at least substantially surrounded by absorbent paper free of lubricating material. The simplest way of achieving this structure is to provide such an array of regions of the absorbent paper impregnated with a lubricating material arranged in a substantially uniform manner throughout the sheet of absorbent paper. Such an array may consist of a plurality of lines or a plurality of dots impregnating the sheet of absorbent paper. For added strength in application, it is preferred that the plurality of lines run with the grain of the paper or that the plurality of dots be arranged in columns running substantially along the grain of the absorbent paper. Such an array of impregnated regions may be formed in the paper by a printing, spraying or similar high speed technique. It is particularly advantageous to form these regions in the absorbent paper stock as manufactured in large rolls prior to cutting up the paper to form the individual tissues.

The lubricated tissue of this invention has absorbent paper adjacent each of the regions impregnated with lubricating material in the array, so that a user may both obtain absorbency from the tissue and apply the lubricating material at the same time from the same general part of the tissue. If the areas of the regions impregnated with lubricating material are small relative to the overall dimensions of the tissue, the tissues further will not stick together when stacked together in a conventional tissue package or in roll form, whether prior to cutting up into individual tissues or in the form of a toilet tissue roll.

DETAILED DESCRIPTION OF THE INVENTION

Figure 1:
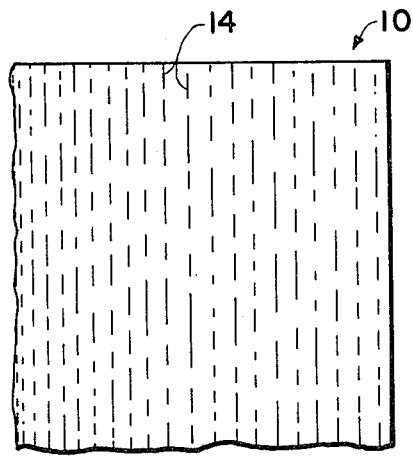
FIG. 1 is a plan view of a portion of a prior art tissue.

Turning now to the drawings, more particularly to FIG. 1, there is shown a conventional prior art tissue 10, which is made of a sheet of absorbent paper 12. Paper 12 has a grain structure 14, running in a generally vertical direction as shown in FIG. 1.

Figure 2:
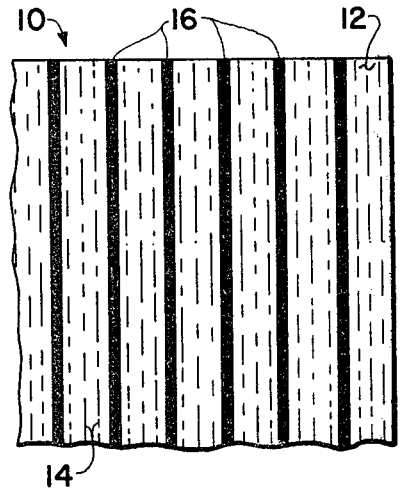
FIG. 2 is a similar plan view of an embodiment of the invention.

FIG. 2 shows a portion of a similar tissue 10 made out of a sheet of absorbent paper 12 having grain structure 14. Paper 12 has a plurality of areas 16 impregnated with a lubricating material and running parallel to the grain structure 14 of the paper 12. The lubricating material may be any of those disclosed in the above-referenced Weiss et al patent, such as petroleum jelly, camphor ice, boric acid ointment, or the material known and used under the trademark Chapstick, or the like. The lubricating material may be medicated or non-medicated, as desired.

While the size of lines 16 is not critical, it is important that there be a large number of the lines 16 over the area of the tissue. Typically, line widths of from about 1/16 to about ¼ inch, with a similar spacing between the lines, should be employed.

While any suitable technique may be used for forming the lines 16 of lubricating material, a printing technique is preferred. The lines 16 should run generally parallel to grain structure 14 of paper 12 for added strength of the paper 12 during the application process. In order that the user need not be concerned about which side of the tissue to use, the pattern of lines 16 should either be coated on both sides of the paper 12 or be allowed to permeate all the way through the paper, so that lubricating material will be available on either side of the paper. While the lubricating material is absorbed by the paper 12, care should be taken not to allow the lubricating material to spread sufficiently to be absorbed by the entire sheet of paper 12. For allowing the lubricating material to be absorbed by paper 12, yet not spread to include all of the paper area, it is best to apply the lubricating material in a thin layer, while hot, to cold or cool paper. By use of such a technique, the lubricating material is absorbed into the paper while hot, but cools rapidly a sufficient amount to solidify so that it will not spread to adjacent areas of the paper 12.

Figure 3:
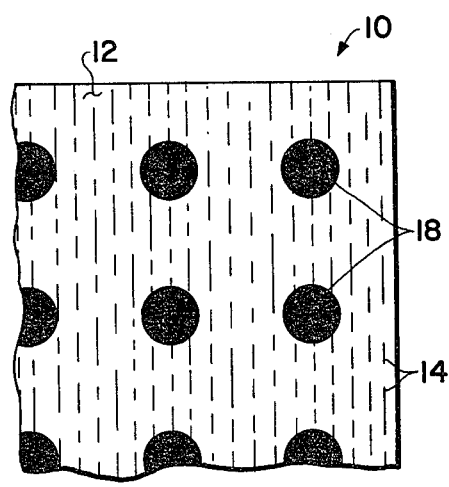
FIG. 3 is a similar plan view of another embodiment of the invention.

FIG. 3 shows a similar tissue 10 made of absorbent paper 12 with grain structure 14 as in FIGS. 1 and 2. The lubricating material is applied to the paper 12 in the form of an array of dots 18. The dots are arranged in a plurality of columns which run generally parallel to the grain structure 14 of paper 12. If desired, the dots 18 in each column may be staggered (not shown) in order to minimize overlapping of the dots on top of one another when paper 12 impregnated with them is rolled up. In both embodiments, it should be noted that the lines 16 and dots 18 are substantially surrounded or completely surrounded, respectively, by absorbent paper 12.

It should now be apparent that an improved lubricating tissue capable of achieving the stated objects of the invention has been provided. By providing a large number of small areas of the tissue impregnated with the lubricating material, the problem of lubricated tissues sticking together as packaged or of paper stock in a roll from which they are fabricated sticking together, is avoided. At the same time, a user can obtain both desired absorbency from the tissue and desired application of the lubricating material to the nose or other irritated portion of the body, without using a different area of the tissue for each purpose.

What is claimed is:

1. A lubricated facial tissue which comprises:
   a facial tissue type sheet of absorbent paper, and a grouped array of regions of said sheet impregnated with lubricant means for applying lubricating material onto a person's skin, each of the regions being at least substantially surrounded by absorbent paper free of lubricating material, said grouped array has a major and a minor dimension and said sheet has a grain, the major dimension of said grouped array lying substantially along the grain, said grouped array of regions being exposed and extending horizontally and vertically across a surface portion of said sheet.

2. The tissue of claim 1 in which regions of said grouped array comprise a plurality of lines running substantially along the grain of said sheet.

3. A lubricated facial tissue which comprises; a facial tissue type sheet of absorbent paper, and a grouped array of regions of said sheet impregnated with lubricant means for applying lubricating material onto a person's skin, each of the regions being at least substantially surrounded by absorbent paper free of lubricating material, said grouped array has a major and a minor dimension and said sheet has a grain, the major dimension of said grouped array lying substantially along the grain, said grouped array of regions being exposed and extending horizontally and vertically across a surface portion of said tissue, the regions of said grouped array comprise a plurality of at least generally circular areas arranged in columns extending substantially along the grain of said sheet.

4. A lubricated facial tissue which comprises:
   a facial tissue type sheet of absorbent paper, and
   a grouped array of regions of said sheet impregnated with a lubricant means for applying lubricating material onto a person's skin, each of the regions being at least substantially surrounded by absorbent paper free of lubricating material, said grouped array of regions being exposed and extending horizontally and vertically across a surface portion of said sheet.

* * * * *